United States Patent [19]

Wilhelm

[11] 4,038,313
[45] July 26, 1977

[54] CYCLOALKYLUREIDO PHENOXY PROPANOLAMINES

[75] Inventor: Max Wilhelm, Watchung, N.J.

[73] Assignee: Ciba-Geigy Corporation, Ardlsey, N.Y.

[21] Appl. No.: 639,683

[22] Filed: Dec. 11, 1975

Related U.S. Application Data

[63] Continuation of Ser. No. 361,373, May 17, 1973, Pat. No. 3,935,259, which is a continuation-in-part of Ser. No. 101,393, Dec. 24, 1970, abandoned.

[30] Foreign Application Priority Data

Jan. 8, 1970 Switzerland .............................. 204/70
Nov. 13, 1970 Switzerland ........................ 16788/70

[51] Int. Cl.$^2$ .................... A61K 31/17; C07C 127/19; C07C 127/15
[52] U.S. Cl. ............................. 260/553 A; 260/343.7; 260/501.17; 424/280; 424/316; 424/322
[58] Field of Search ........... 260/553 A, 501.17, 570.7, 260/343.7

[56] References Cited

U.S. PATENT DOCUMENTS

| | | | |
|---|---|---|---|
| 3,408,387 | 10/1968 | Howe et al. | 260/556 AR X |
| 3,574,749 | 4/1971 | Howe et al. | 260/558 A X |
| 3,644,520 | 2/1972 | Hartley et al. | 260/553 A X |
| 3,660,486 | 5/1972 | Thiele | 260/553 A |
| 3,663,607 | 5/1972 | Barrett | 260/501.17 |
| 3,689,524 | 9/1972 | Jack et al. | 260/553 A X |
| 3,755,413 | 8/1973 | Köppe et al. | 260/562 A X |
| 3,925,446 | 12/1975 | Köppe et al. | 260/553 A X |
| 3,928,412 | 12/1975 | Smith | 260/553 A X |
| 3,930,016 | 12/1975 | Berntsson et al. | 424/330 X |
| 3,944,611 | 3/1976 | Smith | 260/553 A X |
| 3,959,369 | 5/1976 | Smith | 260/553 A X |

FOREIGN PATENT DOCUMENTS

| | | | |
|---|---|---|---|
| 2,040,441 | 2/1971 | Germany | 260/553 A |
| 7,100,178 | 7/1971 | Netherlands | |
| 1,393,675 | 5/1975 | United Kingdom | 260/553 R |

OTHER PUBLICATIONS

Smith, CA 78:71716j (1973).

*Primary Examiner* — Allen B. Curtis
*Assistant Examiner* — Thomas A. Waltz
*Attorney, Agent, or Firm* — Joseph G. Kolodny; John J. Maitner; Theodore O. Groeger

[57] ABSTRACT

Compounds selected from the group consisting of amines of the formula I

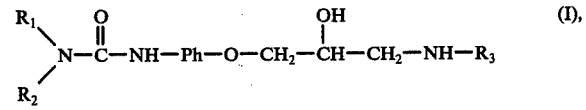

in which $R_1$ and $R_2$ stand for a member selected from lower alkyl, lower alkenyl, cycloalkyl having 4 to 7 ring members, phenyl-lower alkyl, phenyl-lower alkyl substituted in the phenyl residue by a member selected from lower alkyl, lower alkoxy, halogen and trifluoromethyl, lower alkylene, oxa-lower alkylene, aza-lower alkylene and thia-lower alkylene, and one of $R_1$ and $R_2$ stands for hydrogen and the other has the above meanings, Ph stands for a member selected from meta- and para-phenylene and meta- and para-phenylene substituted by a member selected from lower alkyl, lower alkenyl, lower alkinyl, mercapto-lower alkyl, hydroxy-lower alkyl, phenyl, cyano, hydrogen, halogen, lower alkoxy, lower alkenyloxy, lower alkinyloxy, mono-, di and trihalogeno-lower alkyl, cycloalkyl having 5 to 7 ring members and phenoxy, and $R_3$ stands for a member selected from lower alkyl and cycloalkyl having 5 to 7 ring members, and their condensation product with aldehydes and ketones, and their salts are useful as agents for the inhibition of the cardiac $\beta$-receptors.

1 Claim, No Drawings

CYCLOALKYLUREIDO PHENOXY PROPANOLAMINES

CROSS-REFERENCES TO OTHER APPLICATIONS

This application is a continuation of application Ser. No. 361,373, filed May 19, 1973, now U.S. Pat. No. 3,935,259, which, in turn, is a continuation -in- part of my copending application Ser. No. 101,393, filed Dec. 24, 1970 (now abandoned). The invention relates to new amines of formula I

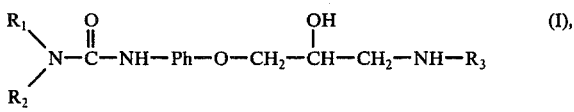

wherein $R_1$ represents hydrogen or an optionally substituted monovalent hydrocarbon radical of aliphatic character, $R_2$ represents an optionally substituted monovalent hydrocarbon radical of aliphatic character, or $R_1$ and $R_2$ together represent a divalent hydrocarbon radical of aliphatic character, which can optionally be interrupted by heteroatoms and/or substituted, Ph represents a meta- or preferably para-phenylene radical and $R_3$ represents an aliphatic or cycloaliphatic radical, and their condensation products with aldehydes or ketones, as well as processes for the manufacture of these compounds.

A radical of aliphatic character is a radical in which the first carbon atom bonded to the nitrogen atom does not belong to an aromatic system.

Optionally substituted monovalent hydrocarbon radicals of aliphatic character $R_1$ and $R_2$, which can be identical or different, are for example optionally substituted aliphatic, cycloaliphatic, cycloaliphatic-aliphatic or araliphatic hydrocarbon radicals such as for example alkyl, hydroxyalkyl, alkenyl, alkinyl, cycloalkyl, cycloalkenyl, cycloalkyl-alkyl or cycloalkyl-alkenyl, cycloalkenyl-alkyl or cycloalkenyl-alkenyl, aralkyl or aralkenyl, for example phenyl-lower alkyl or phenyl-lower alkenyl, and especially the lower radicals of the indicated nature, the term lower radicals being used to describe those containing up to 7 C atoms.

Lower alkyl radicals are for example methyl, ethyl, n-propyl or isopropyl, or straight-chain or branched butyl, pentyl or hexyl, which can be bonded in any desired position.

Lower hydroxyalkyl radicals are for example radicals in which the alkyl parts have the above significance, such as 2-hydroxyethyl, 3-hydroxy-n-propyl, 2,3-dihydroxy-n-propyl or 3-hydroxy-n-butyl.

Lower alkenyl radicals are for examples allyl or methallyl.

Lower alkinyl radicals are especially propargyl radicals.

Cycloalkyl or cycloalkenyl radicals are for example optionally lower-alkylated cycloalkyl or cycloalkenyl radicals with 3-7, especially 5-7, ring members, such as optionally lower-alkylated cyclopentyl, cyclohexyl, cycloheptyl, cyclopentenyl, cyclohexenyl, for example 1- or 3-cyclohexenyl, or cycloheptenyl.

Cycloalkyl-alkyl or cycloalkyl-alkenyl radicals are above all those in which the alkyl or alkenyl parts are lower alkyl or alkenyl radicals, especially those mentioned above, and in which the cycloalkyl parts preferably have the significance given above for cycloalkyl radicals, such as 1- or 2-cyclopentyl-ethyl, 1-, 2- or 3-cyclohexylpropyl, cycloheptyl-methyl or 1- or 2-cyclohexyl-ethyl.

Cycloalkenyl-alkyl or cycloalkenyl-alkenyl radicals are above all those in which the alkyl and alkenyl parts are lower alkyl or alkenyl radicals, especially those mentioned above, and in which the cycloalkenyl parts preferably have the significance given above for cycloalkenyl radicals, such as 1- or 2-cyclopent-3-enylethyl, 1- or 2-cyclohex-1-enyl-ethyl, cyclohept-1-enylmethyl or 1- or 2-cyclohex-3-enyl-ethyl.

Phenyl lower alkyl radicals are for example those in which the lower alkyl parts have the above significance, such as 1- or 2-phenylethyl or benzyl, with the phenyl parts optionally being substituted by lower alkyl, especially those mentioned above, lower alkoxy radicals, halogen atoms or trifluoromethyl radicals, whilst phenyl-lower alkenyl radicals are for example those in which the lower alkenyl radicals have the above significance, such as 1- or 2-phenylethenyl or cinnamyl, with the phenyl parts optionally being substituted as indicated above for the phenyl-lower alkyl radicals.

Lower alkoxy radicals are for example methoxy, ethoxy, propoxy, isopropoxy, butoxy, amyloxy or methylenedioxy.

Halogen atoms are especially fluorine, chlorine or bromine.

Divalent hydrocarbon radicals of aliphatic character, which are conjointly represented by $R_1$ and $R_2$, and which can optionally be interrupted by hetero-atoms and/or substituted, are preferably lower alkenyl radicals, which can be straight-chain or branched, and above all possess 4-6 chain carbon atoms if the carbon chain is uninterrupted or 4 or 5 chain carbon atoms if the carbon chain is interrupted by hetero-atoms. Possible hetero-atoms are especially oxygen, sulphur and nitrogen. Examples of such radicals are butylene-(1,4), pentylene-(1,5), hexylene-(1,5), hexylene-(2,5),hexylene-(1,6), heptylene-(1,6), 3-oxa-pentylene-(1,5), 3-oxa-hexylene-(1,6), 3-thia-pentylene-(1,5), 2,4-dimethyl-3-thiapentylene-(1,5), 3-azapentylene-(1,5), 3-lower alkyl-3-azapentylene-(1,5), such as 3-methyl-3-aza-pentylene-(1,5) or 3-azahexylene-(1,6).

Meta- or para-phenylene radicals Ph can be unsubstituted or have one, two or more substituents. Substituents are above all lower alkyl, lower alkenyl, lower alkinyl, cycloalkyl, phenyl-lower alkyl and lower alkoxy, especially those mentioned above, phenyl, lower alkenyloxy, lower alkinyloxy, halogen, especially those mentioned above, as well as substituted lower alkyl, phenoxy, trifluoromethyl and/or nitrile.

Lower alkenyloxy radicals are for example allyloxy or methallyloxy and lower alkinyloxy radicals are above all propargyloxy.

Substituted lower alkyl radicals are preferably lower alkyl radicals, especially those mentioned above, which are substituted by hydroxyl, lower alkoxy, especially those mentioned above, optionally substituted mercapto, such as free mercapto or lower alkylmercapto, for example methylmercapto or ethylmercapto, or halogen, especially those mentioned above. Such radicals are for example hydroxy-lower alkyl, lower alkylmercapto-lower alkyl and halogen-lower alkyl, such as 2-hydroxyethyl, 2-methoxyethyl, 2-mercaptoethyl, methylmercaptomethyl and 2,2-dichlorethyl.

The aliphatic or cycloaliphatic radical $R_3$ is preferably an aliphatic or cycloaliphatic hydrocarbon radical, especially one of those mentioned above, as well as lower alkoxy-lower alkyl or halogen-lower alkyl, such as those mentioned above, as well as cycloalkyl radicals interrupted by hetero-atoms.

Cycloalkyl radicals interrupted by hetero-atoms are especially cycloalkyl radicals interrupted by oxygen, sulphur or nitrogen, such as tetrahydrofuryl, tetrahydropyranyl, tetrahydrothienyl, tetrahydrothiapyranyl, piperidyl or pyrrolidinyl.

Condensation products of compounds of formula I with aldehydes or ketones are especially compounds of formula II

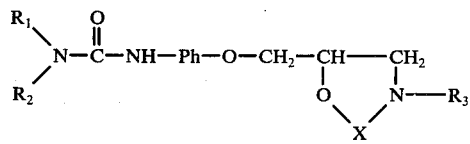 (II)

wherein $R_1$, $R_2$, Ph and $R_3$ have the above significance and X represents an alkylidene radical.

The alkylidene radical X is especially a lower alkylidene radical, such as ethylidene, n-propylidene, isopropylidene, or straight-chain or branched butylidene or pentylidene, or above all methylene. The alkylidene radicals mentioned, and especially the methylene radical, can carry one or more substituents, such as cycloaliphatic hydrocarbon radicals, especially those mentioned above, or aromatic radicals.

Aromatic radicals are above all phenyl radicals which are optionally substituted as indicated above for the phenyl parts of phenyl-lower alkyl radicals, or heterocyclic aromatic radicals, such as furyl, thienyl, pyrryl and above all pyridyl.

The new compounds possess valuable pharmacological properties. Thus they inhibit cardioselective β-receptors as is found in animal experiments, for example on intravenous administration of 0.1 - 1 mg/kg to pentobarbitalnarcotized cats in the isoproterenol-tachycardia test, on intravenous administration of more than 10 mg/kg in narcotized cats through inhibition of the isoproterenol vasodilatation, on the isolated guinea pig heart (according to Langendorff) in a concentration of approximately 0.3 - 3 γ/ml through inhibition of the isoproterenol tachy-cardia (blocking of cardial β-receptors), as also on intravenous administration of approximately 5-30 mg/kg in narcotized cats through blocking of vascular β-receptors.

The new compounds are therefore useful as cardioselective β-receptor blocking agents. The new compounds are however also valuable intermediate products for the manufacture of other useful substances, especially pharmaceutically active compounds.

Compounds to be particularly highlighted are those of formula I, wherein $R_1$ represents hydrogen, lower alkyl, lower alkenyl, cycloalkyl with 4–7 ring members or phenyl-lower alkyl, with the phenyl part of the phenyl-lower alkyl radicals being unsubstituted or substituted by lower alkyl, lower alkoxy, halogen and/or trifluoromethyl, $R_2$ and $R_3$, which are identical or different, each represent lower alkyl, lower alkenyl, cycloalkyl with 4–7 ring members or phenyl-lower alkyl, with the phenyl part of the phenyl-lower alkyl radicals being optionally substituted as indicated for $R_1$, and Ph is a para-phenylene radical, and their condensation products of formula II, wherein X represents ethylidene, isopropylidene or above all methylene, with the methylene radical optionally being substituted by phenyl or pyridyl.

Particularly valuable compounds because of their outstanding pharmacological properties are compounds of formulae III and IV

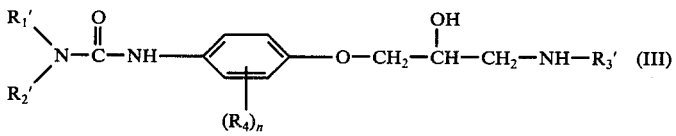 (III)

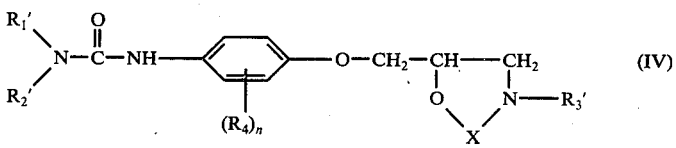 (IV)

wherein $R_1'$ and $R_2'$ each represent lower alkyl, $R_3'$ represents straight-chain or preferably branched lower alkyl, such as especially sec.butyl, tert.butyl or above all isopropyl, or cycloalkyl with 5–7 ring carbon atoms, $n$ represents 1, $R_4$ represents lower alkenyl, lower alkinyl, mercapto-lower alkyl or hydroxy-lower alkyl with in each case up to 4 C-atoms, or represents phenyl, nitrile or preferably hydrogen, halogen, lower alkyl, lower alkoxy, lower alkenyloxy, lower alkinyloxy, mono-, di- or tri-halogen-lower alkyl with in each case up to 4 C atoms, cycloalkyl with 5–7 ring carbon atoms or phenoxy, and $X'$ in compounds of formula IV represents unsubstituted methylene or preferably methylene substituted by phenyl or pyridyl, and amongst compounds of formula III, especially those in which $R_1'$, $R_2'$ and $R_3'$ have the above significance, $n$ represents 1, and $R_4$ represents a hydrogen atom, or preferably a halogen atom, especially chlorine or bromine, such as 1-[(p-N',N'-dimethyl-ureido)-phenoxy]2-hydroxy-3-isopropylamino-propane, 1-[(N',N'-dimethyl-ureido)-phenoxy]-2-hydroxy-3-isopropylamino-propane, 1-[o-allyl-p-N',N'-dimethylureido)-phenoxy]-2-hydroxy-3-isopropylamino-propane, 1-[(o-methoxy-p-N',N'-dimethylureido)-phenoxy]-2-hydroxy-3-isopropylamino-propane, 1-[(o-allyloxy-p-N',N'-dimethylureido)-phenoxy]-2-hydroxy-3-isopropylamino-propane, 1-[(p-N',N'-(3-oxapentylene-1,5)-ureido)-phenoxy]-2-hydroxy-3-isopropylamino-propane and especially 1-[(o-chloro-p-N'-N'-dimethylureido)-phenoxy]-2-hydroxy-3-isopropylamino-propane, which for example when intravenously administered 0.1–1 mg/kg to pentobarbital-narcotized cats inhibit the isoproterenol tachycardia (0.5 γ/kg administered intravenously and on intravenous administration of over 10 mg/kg to pentobarbital-narcotized cats inhibit the isoproterenol-vasodilatation (0.5 γ/kg administered intravenously) and also, in concentrations of 0.3 - 3 γ/ml, inhibit the isoproterenol-tachycardia (0.005 γ/ml) (blocking of cardial β-receptors) on the isolated guineapig heart (according to Langendorff), and block vascular β-receptors on intraveneous administration of 5-30 of mg/kg on narcotized cats.

The new compounds are obtained according to methods which are in themselves known.

Thus it is for example possible to react a compound of formula V

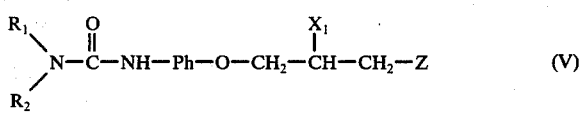

wherein $R_1$, $R_2$ and Ph have the above significance, $X_1$ represents the hydroxyl group and Z represents a reactive esterified hydroxyl group, or $X_1$ and Z together form an epoxy group, with an amine of formula $NH_2$—$R_3$, wherein $R_3$ has the above significance.

A reactive esterified hydroxyl group is especially a hydroxyl group esterified by a strong inorganic or organic acid, above all a hydrohalic acid, such as hydrochloric acid, hydrobromic acid or hydriodic acid, and also sulphuric acid or a strong organic sulphonic acid, such as a strong aromatic sulphonic acid, for example benzenesulphonic acid, 4-bromobenzenesulphonic acid or 4-toluenesulphonic acid. Thus Z especially represents chlorine, bromine or iodine.

This reaction is carried out in the usual manner. When using a reactive ester as the starting material, the process is preferably carried out in the presence of a basic condensation agent and/or with an excess of amine.

It is furthermore possible to react a compound of formula VI

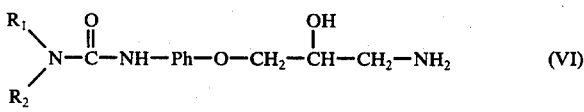

wherein $R_1$, $R_2$ and Ph have the above significance, or a condensation product thereof with an aldehyde or ketone, for example a condensation product of formula VII

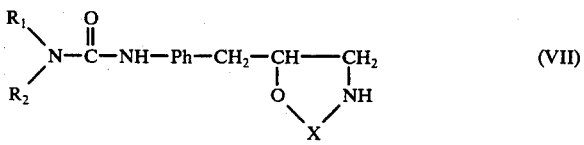

wherein $R_1$, $R_2$, X and Ph have the above significance, with a compound of formula Z—$R_3$ wherein Z and $R_3$ have the above significance.

This reaction is carried out in the usual manner, preferably in the presence of a basic condensation agent and/or with an excess of amine. Suitable basic condensation agents are, for example, alkali alcoholates, especially sodium or potassium alcoholate, or alkali carbonates, such as sodium or potassium carbonate.

It is furthermore possible to react a compound of formula VIII

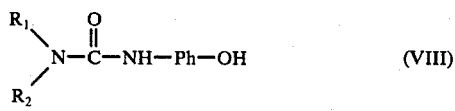

wherein $R_1$, $R_2$ and Ph have the above significance, with a compound of formula IX

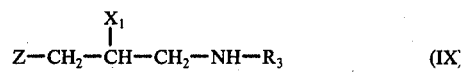

wherein Z, $X_1$ and $R_3$ have the above significance, or with a condensation product of a compound of formula IX, wherein $X_1$ represents hydroxyl and Z represents a reactive esterified hydroxyl group, with an aldehyde or ketone, for example one of formula X

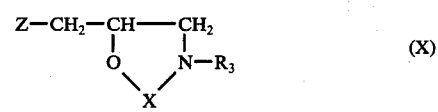

wherein Z, $R_3$ and X have the above significance.

This reaction is carried out in the usual manner. If reactive esters are used as the starting material, the compound of formula VIII can preferably be used in the form of its metal phenolate, such as alkali phenolate, for example sodium phenolate, or the process is carried out in the presence of an acid-binding agent, especially a condensation agent, which can form a salt with the compound of formula VIII, such as an alkali alcoholate.

It is furthermore possible, in a compound of formula I wherein $R_1$, $R_2$, $R_3$ and Ph have the above significance and which possesses a removable radical on the nitrogen atom of the amino group and/or on the hydroxyl group, to remove this radical or radicals.

Such removable radicals are especially radicals removable by hydrolysis or hydrogenolysis.

Radicals removable by hydrolysis are for example acyl radicals, for example oxycarbonyl radicals, such as alkoxycarbonyl radicals, for example the tert.-butoxycarbonyl radical, aralkoxycarbonyl radicals, for example a carbobenzoxy radical, and especially lower alkanoyl radicals or aryloyl radicals, for example the acetyl radical or a benzoyl radical.

Compounds with radicals which can be removed by hydrolysis are for example also compounds of formula XI

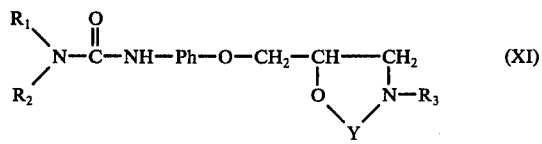

wherein $R_1$, $R_2$, $R_3$ and Ph have the above significance and Y represents a carbonyl or thiocarbonyl radical.

The hydrolysis is carried out in the usual manner by means of hydrolysing agents and, for example, in the presence of basic agents or, especially when using compounds of formula XI as the starting material, of acid agents. Such acid agents are for example dilute inorganic acids, such as sulphuric acid or a hydrohalic acid, such as one of those mentioned above.

Radicals removable by hydrogenolysis are for example α-aralkyl radicals, such as benzyl radicals, or aryloxycarbonyl radicals, such as phenoxycarbonyl radicals, which can be split off by hydrogenolysis in the usual manner, especially by catalytically activated hydrogen, such as by hydrogen in the presence of a hydrogenation catalyst, for example palladium or platinum. Further radicals which are removable by hydrogenolysis are for example β-halogen-ethoxycarbonyl radicals, such as the 2,2,2-trichlorethoxycarbonyl radical or the 2-iodethoxycarbonyl or 2,2,2-tribromethoxycarbonyl radical, which can be removed in the usual manner, especially by nascent hydrogen. Nascent hydrogen can herein be obtained by the action of metal or metal alloys on agents which yield hydrogen, such as carboxylic acids, alcohols or water, and in particular zinc or zinc alloys together with acetic acid can be used. The hydrogenolysis of β-halogen-ethoxycarbonyl radicals can preferably be effected by chromium-II compounds, such as chromium-II chloride or chromium-II acetate. In carrying out the hydrogenolysis care must be taken that other reducible groups, above all the urea group, and not attacked.

It is furthermore possible to reduce a Schiff base of formulae XII or XIII

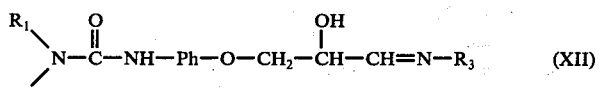

or

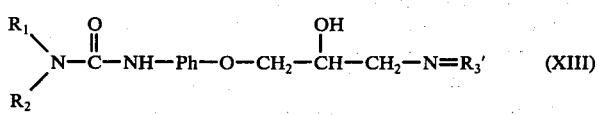

or a ring-tautomer, corresponding to formula XIII, of formula XIV

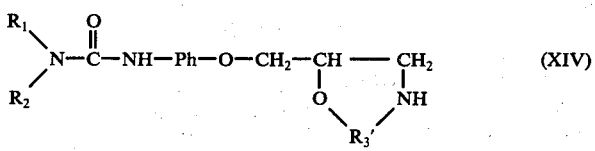

wherein $R_1$, $R_2$, Ph and $R_3$ have the above significance and $R_3'H$ is the same as $R_3$, and wherein compounds of formulae XIII and XIV can also be present alongside one another, or an immonium salt condensation product of a compound of formula XIII with an aldehyde or ketone, for example a compound of formula XV

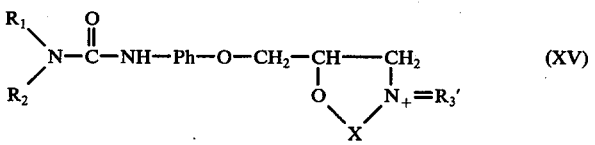

wherein $R_1$, $R_2$, $R_3'$, Ph and X have the above significance.

This reduction is carried out in the usual manner, for example with a di-light metal hydride, such as sodium borohydride, or by catalytic hydrogenation, such as with hydrogen in the presence of palladium, platinum oxide or Raney nickel. During the reduction, care must be taken that other reducible groups, above all the urea group, are not attacked.

It is furthermore possible to reduce the 2-oxo group in a compound of formula XVI

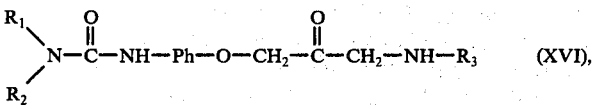

wherein $R_1$, $R_2$, $R_3$ and Ph have the above significance, to a hydroxyl group.

This reduction is carried out in the usual manner, especially using a di-light metal hydride, such as one of those mentioned above, or according to the method of Meerwein-Pondorf-Verley or a modification thereof, especially with an alkanol as a reagent and as a solvent, such as isopropanol, and with a metal alkanolate, preferably a metal alkanolate corresponding to the alkanol, such as a metal isopropanolate, for example aluminium isopropanolate.

It is furthermore possible to react a reactive acid derivative of a carbamic acid of formula XVII

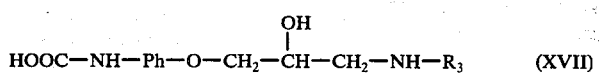

wherein Ph and $R_3$ have the above significance, or one of its condensation products with an aldehyde or ketone, with an amine of formula $R_1$—NH—$R_2$, wherein $R_1$ and $R_2$ have the above significance.

A reactive acid derivative of such a carbamic acid is for example a lower alkyl ester or above all a phenyl ester, an acid halide, such as an acid chloride, or especially an internal anhydride, such as an isocyanate.

This reaction is carried out in the usual manner, especially using an excess of amine, and optionally in a solvent and at elevated temperature, preferably above 100° C.

In resulting compounds, substituents can be modified, introduced or removed in the usual manner within the framework of the final substances, on resulting compounds can be converted into other final substances in the usual manner.

Thus condensation products of formula II can be obtained by reacting an amine of formula I with an aldehyde or ketone of formula X=O, wherein X has the above significance, or with a reactive carbonyl derivative thereof.

Reactive carbonyl derivatives are above all acetals, ketals, hemithioketals, thioketals, especially dimethyl- or diethyl-acetals, -ketals or -thioketals, or acylals, especially those with acetic acid or with a hydrohalic acid, has the above significance.

This reaction is carried out in the usual manner, in the presence or absence of a solvent, at room temperature or preferably at elevated temperature, if necessary in the presence of a condensation agent, especially an acid condensation agent.

In a corresponding manner, a condensation product of formula II can be converted into an amine of formula I in the usual way by hydrolysis, especially in a basic medium or preferably in an acid medium.

It is furthermore possible, in resulting compounds which contain a C—C double bond or triple bond, to convert the C—C double bond or triple bond into a C—C single bond by catalytic hydrogenation, such as by hydrogen in the presence of a hydrogenation catalyst, for example nickel, platinum or palladium, such as Raney nickel, platinum black or palladium on active charcoal. Here care must be taken that other reducible groups, above all the urea group, are not attacked.

In resulting compounds which contain a C—C triple bond, the latter can furthermore be hydrogenated merely to a C—C double bond and, if desired, stereospecifically to a C—C-cis or C—C-trans double bond.

The hydrogenation of a C—C triple bond to a C—C double bond can for example be carried out by hydrogenation with 1 mol of hydrogen in the presence of a less active hydrogenation catalyst, such as iron or palladium, for example Raney iron or palladium on barium sulphate, especially at elevated temperature. The hydrogenation to a C—C-cis double bond can for example be carried out by means of 1 mol of hydrogen in the presence of a deactivated catalyst, such as palladium on animal charcoal in the presence of quinoline, palladium on calcium carbonate in the presence of lead salts, or Raney nickel. The hydrogenation to a C—C-trans double bond can for example be carried out by means of sodium in liquid ammonia, with short reaction times and no excess of reducing agent being used, especially taking the urea group into account, and with an ammonium halide, such as ammonium chloride, optionally being added as the catalyst.

The reactions mentioned are carried out in the usual manner in the presence or absence of diluents, condensation agents and/or catalytic agents, at lowered, ordinary or elevated temperature, optionally in a closed vessel.

Depending on the process conditions and starting substances, the final substances are obtained in the free form or in the form of their acid addition salts, which are also included in the invention. Thus for example basic, neutral or mixed salts, and where relevant also hemihydrates, monohydrates, sesquihydrates or polyhydrates thereof, can be obtained. The acid addition salts of the new compounds can be converted into the free compound in a manner which is in itself known, for example with basic agents, such as alkalis or ion exchangers. On the other hand, the resulting free bases can form salts with organic or inorganic acids. In order to manufacture acid addition salts, such acids are especially used as are suitable for forming therapeutically usable salts. As such acids there may for example be mentioned: hydrohalic acids, sulphuric acids, phosphoric acids, nitric acid, perchloric acid, aliphatic, alicyclic, aromatic or heterocyclic carboxylic or sulphonic acids, such as formic, acetic, propionic, succinic, glycollic, lactic, malic, tartaric, citric, ascorbic, maleic, hydroxymaleic or pyruvic acid; phenylacetic, benzoic, p-aminobenzoic, anthranilic, p-hydroxybenzoic, salicylic or p-aminosalicylic acid, embonic acid, methanesulphonic, ethanesulphonic, hydroxyethanesulphonic and ethylenesulphonic acid; halogenobenzenesulphonic, toluenesulphonic, naphthalenesulphonic or sulphanilic acid; methionine, tryptophan, lysine or arginine.

These or other salts of the new compounds, such as for example the picrates, can also serve for the purification of the resulting free bases, by converting the free bases into salts, separating these off and again liberating the bases from the salts. In view of the close relationships between the new compounds in the free form and in the form of their salts, the free compounds are, in the preceding and following text, where appropriate also to be understood to include the corresponding salts as regards sense and purpose.

The invention also relates to those embodiments of the process according to which one starts from a compound obtainable as an intermediate product at any stage of the process and carries out the missing process stages, or stops the process at any stage, or in which a starting substance is formed under the reaction conditions, or in which a reagent is optionally present in the form of its salts.

Thus it is possible to react an aldehyde of formula XVIII

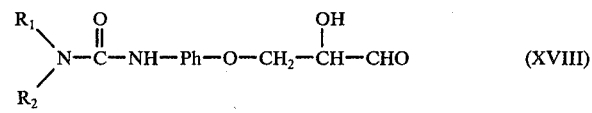

$$\begin{matrix} R_1 \\ \phantom{R}\diagdown \\ \phantom{RR}N-\overset{O}{\overset{\|}{C}}-NH-Ph-O-CH_2-\overset{OH}{\overset{|}{CH}}-CHO \\ \phantom{R}\diagup \\ R_2 \end{matrix} \qquad (XVIII)$$

wherein $R_1$, $R_2$ and Ph have the above significance, with an amine of formula $H_2N-R_3$, wherein $R_3$ has the above significance, in the presence of a suitable reducing agent such as one of those mentioned above. Here a compound of formula XII is obtained as an intermediate product and this is then reduced in accordance with the invention.

It is furthermore possible in a suitable manner to react an amine of formula VI with an aldehyde or ketone of formula $O=R_3'$, wherein $R_3'$ has the above significance, in the presence of a suitable reducing agent, such as one of those mentioned above. Here a compound of formula XIII or XIV is obtained as an intermediate product and this is then reduced in accordance with the invention.

The new compounds can, to the extent that they possess asymmetric carbon atoms, and depending on the choice of the starting substances and working methods, be present as optical antipodes or racemates or, to the extent that they contain at least two asymmetric carbon atoms, also as isomer mixtures (racemate mixtures).

Resulting isomer mixtures (racemate mixtures) can be resolved into the two stereoisomeric (diastereomeric) pure racemates on the basis of the physico-chemical differences of the constituents in a known manner, for example by chromatography and/or fractional crystallisation.

Resulting racemates can be resolved according to known methods, for example by recrystallisation from an optically active solvent, with the aid of micro-organisms or by reaction with an optically active acid which forms salts with the racemic compound and separation of the salts obtained in this manner, for example on the basis of their different solubilities, into the diastereomers, from which the antipodes can be liberated by the action of suitable agents. Particularly customary optically active acids are for example the D- and L-forms of tartaric acid, di-o-toluyltartaric acid, malic acid, mandelic acid, camphorsulphonic acid or quinic acid. Advantageously the more active of the two antipodes is isolated.

Appropriately, such starting substances are used for carrying out the reactions according to the invention as lead to the initially particularly mentioned groups of final substances and particularly to the final substances which have been especially described or highlighted.

The starting substances are known or can, if they are new, be obtained according to methods which are in themselves known.

The new compounds can be used as medicines, for example in the form of pharmaceutical preparations, in which they or their salts are present mixed with a pharmaceutical, organic or inorganic, solid or liquid carriers which is for example suitable for enternal or parenteral administration. Possible substances for forming the carriers are those which do not react with the new compounds, such as for example water, gelatine, lactose, starch, magnesium stearate, talc vegetable oils, benzyl alcohols, gum, polyalkylene glycols, white petroleum jelly, cholesterol or other known medicinal carriers.

The pharmaceutical preparations can for example be in the form of tablets, dragees, capsules, suppositories, ointments or creams, or in a liquid form as solutions (for example as an elixir or syrup), suspensions or emulsions. They are optionally sterilised and/or contain auxiliary substances, such as preservatives, stabilisers, wetting agents or emulsifiers, salts for regulating the osmotic pressure or buffers. They can also contain yet further therapeutically valuable substances. The preparations, which can also be used in veterinary medicine, are formulated according to usual methods.

The examples which follow explain the invention without however restricting it.

EXAMPLE 1

A solution of 40 g of 1-[o-chloro-p-(N',N'-dimethylureido)-phenoxy]-2,3-epoxy-propane and 40 g of isopropylamine in 40 ml of ethanol is heated to boiling for 4 hours. Thereafter the mixture is concentrated by evaporation in vacuo and the residue is dissolved in 2 N hydrochloric acid. After extraction with ether, the hydrochloric acid layer is separated off and rendered alkaline by adding concentrated sodium hydroxide solution. The base which has separated out is extracted by shaking with methylene chloride. After evaporation of the solvent and after recrystallisation of the residue from ethyl acetate, the 1-[o-chloro-p-(N',N'-dimethylureido)-phenyoxy]-2-hydroxy-3-isopropylamino-propane of formula

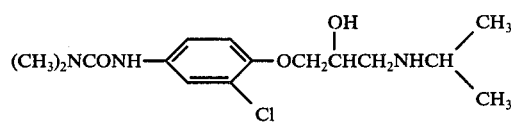

is obtained in crystals of melting point 130° C.

The cyclohexylsulphamate melts at 146°–150° C.

The epoxide used as the starting product can be manufactured as follows:

50 g of dimethylcarbamic acid chloride are added dropwise at room temperature to a solution of 63 g of 3-chloro-4-hydroxy-aniline in 300 ml of pyridine, whilst stirring and the mixture is left to stand for 12 hours. Thereafter 2 N hydrochloric acid is added until a pH value of 5 reached, after which the N,N-dimethyl-N'-(3-chloro-4-hydroxy-phenyl)-urea precipitates. The compound melts at 202°–203° C.

45 g of the phenol are now heated for 15 hours under reflux with 45 g of epichlorohydrin and 45 g of potassium hydroxide in 450 ml of acetone. Thereafter the potassium hydroxide is filtered off and the solvent is evaporated off. The residue is dissolved in methylene chloride and extracted by shaking with 2 N sodium hydroxide solution. After evaporation of the solvent, the crude 1-[o-chloro-p-(N',N'-dimethylureido)-phenoxy]-2,3-epoxy-propane remains, which is used for the above reaction.

EXAMPLE 2

10 g of 1-[p-(N',N'-dimethylureido)-phenoxy]-2,3-epoxypropane are warmed for 4 hours at 90° C with 10 g of isopropylamine in 10 ml of ethanol. Thereafter the excess amine as well as the solvent are evaporated off in vacuo. The residue is dissolved in 2 N hydrochloric acid, the undissolved constituents are filtered off and the solution extracted with methylene chloride. The aqueous phase is rendered alkaline by adding 2 N sodium hydroxide solution and is thereafter extracted with methylene chloride. After evaporation of the solvent, 1-[p-(N',N'-dimethylureido)-phenoxy]-2-hydroxy-3-isopropylamino-propane of formula

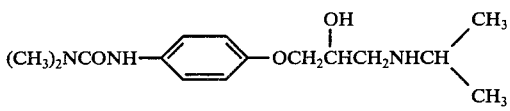

remains, which after recrystallisation from benzene melts at 138°–139° C.

The epoxide used as the starting product can be manufactured as follows:

12 g of dimethylcarbamoyl chloride are added to a solution of 20 g of p-benzyloxy-aniline in 100 ml of pyridine and the mixture is left to stand for 2 days. On addition of water, the N,N-dimethyl-N'-(p-benzyloxy-phenyl)-urea precipitates; it melts at 155°–158° C after sublimation.

20 g of this urea are dissolved in 200 ml of ethanol and hydrogenated after addition of 2 g of palladium-charcoal (10 per cent strength). When the uptake of hydrogen has ended, the mixture is concentrated by evaporation on vacuo and the residue is dissolved in 2 N sodium hydroxide solution. The undissolved constituents are extracted with ether and the aqueous layer is rendered acid by adding 5 N hydrochloric acid. N,N-dimethyl-N'-(p-hydroxyphenyl)-urea precipitates; it melts at 203°–205° C after recrystallisation from isopropanol.

20 g of the phenol are heated for 10 hours with 20 g of potassium hydroxide and 20 g of epichlorhydrin in 200 ml of acetone, whilst stirring. Thereafter the potassium hydroxide is filtered off and the filtrate is concentrated by evaporation. The residue is dissolved in methylene chloride and extracted with 2 N sodium hydroxide solution. After evaporation of the methylene chloride, the crude 1-[p-(N',N'-dimethylureido)-phenoxy]-2,3-epoxy-propane remains as an oil.

EXAMPLE 3

A solution of 1-[o-allyl-p-(N',N'-dimethylureido)-phenoxy]-2,3-epoxypropane (15 g) and isopropylamine (15 g) in 20 ml of ethanol is heated for 4 hours. Thereafter the reaction mixture is evaporated in vacuo, the residue dissolved in 2N-hydrochloric acid, and filtered. The filtrate is rendered alkaline by addition of concentrated sodium hydroxide solution. An oil is precipitated that is extracted with methylene chloride. After the solution has been dried and the solvent evaporated, there remains 1-[o-allyl-p-(N',N'-dimethylureido)-phenoxy]-2-hydroxy-3-isopropylaminopropane of formula

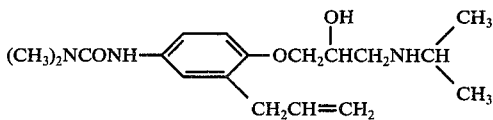

which after recrystallization from benzene-petroleum ether melts at 110°–112° C.

The epoxide used as starting material can be prepared in the following way:

To 2-allyl-4-amino-phenol (15 g) in 50 ml of pyridine is added dimethyl-carbamoyl chloride (12 g) and the mixture is left to stand for 12 hours at 25° C. On addition of 200 ml of 2N hydrochloric acid, extraction with methylene chloride is effected. The extract is evaporated to dryness in vacuo. The residue is dissolved in 2N sodium hydroxide solution, the resulting solution treated with charcoal and adjusted to a pH of 9 by addition of hydrochloric acid. The precipitated constituents are filtered off, the filtrate rendered acid. 2-Allyl-4-(N',N'-dimethylureido)-phenol is precipitated, which after recrystallization from ethyl acetate-pentane melts at 125°–127° C.

12 g of the phenol is heated to boiling for 12 hours with 12 g of epichlorohydrin and 12 g of potassium carbonate in 75 ml of acetone. Thereafter the solid constituents are filtered off and filtrate is evaporated in vacuo. The residue is dissolved in methylene chloride and extracted with sodium hydroxide solution. After evaporation of the solvent, the crude 1-[o-allyl-p-(N',N'-dimethylureido)-phenoxy]-2,3-epoxypropane remains as an oil.

EXAMPLE 4

A mixture of 30 g 1-[m-(N',N'-dimethylureido)-phenoxy]-2,3-epoxy-propane, 30 g isopropylamine and 30 ml ethanol is heated to 60° for 4 hours and then evaporated to dryness in vacuo. The residue is dissolved in 2N-acetic acid and extracted with ether. After separation of the water phase the same is rendered alkaline by addition of sodium hydroxide solution and extracted with methylene chloride. After evaporation of the solvent the 1-[m-(N',N'-dimethylureido)-phenoxy]-2-hydroxy-3-isopropylamino-propane of the formula

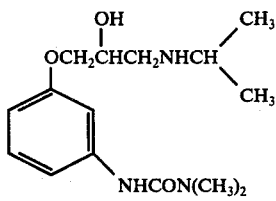

remains, which melts after recrystallization from isopropanol at 130°.

EXAMPLE 5

Tablets containing 20 mg of active substance are manufactured with the following composition:

| | |
|---|---|
| 1-[o-Chloro-p-(N',N'-dimethylureido)-phenoxy]-2-hydroxy-3-isopropylamino-propane | 20 mg |
| Starch | 60 mg |
| Lactose | 50 mg |
| Collodial silica | 5 mg |
| Talc | 9 mg |
| Magnesium stearate | 1 mg |
| | 145 mg |

Tablets containing 20 mg of 1-[p-(N',N'-dimethylureido)-phenoxy]-2-hydroxy-3-isopropylamino-propane can be manufactured in the usual manner with the same composition.

EXAMPLE 6

The following mixture is used to manufacture capsules:

| | |
|---|---|
| 1-[o-Chloro-p-(N',N'-dimethylureido)-phenoxy-2-hydroxy-3-isopropylamino-propane | 2500 g |
| Talc | 80 g |
| colloidal silica | 20 g |

The active substance is intimately mixed with talc and colloidal silica, and the mixture is forced through a sieve (0.5 mm) and filled into hard gelatine capsules in portions of 21 mg.

Capsules can be manufactured in the same manner and with the same composition using 1-[p-(N',N'-dimethylureido)-phenoxy]-2-hydroxy-3-isopropylaminopropane.

EXAMPLE 7

A mixture of 20 g of p-(N',N'-dimethylureido)-phenol, 15 g of 3-isopropylamino-2-hydroxy-1-chloropropane, and 20 g of finely ground potassium carbonate in 250 ml of acetone is stirred at 50° for 5 hours. The solid part of the mixture is filtered off and the acetone solution is evaporated in a vacuum. The residue is dissolved in 100 ml of 2N hydrochloric acid, the undissolved part is filtered off and the remaining mixture is extracted with methylene chloride. The aqueous phase is rendered alkaline by adding 2N sodium hydroxide solution and is extracted with methylene chloride. After the evaporation of the solvent, 1-[p-(N',N'-dimethylureido)-phenoxy]-2-hydroxy-3-isopropylaminopropane is isolated which melts at 138°–139° after recrystallisation from benzene and has the formula

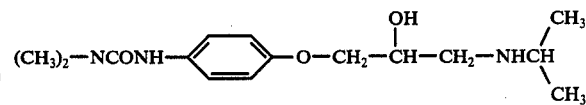

EXAMPLE 8

7 g of 1-[p-(N'-methylureido)-phenoxy]-2-hydroxy-(3-isopropylbenzylamino)-propane in 70 ml of ethanol are hydrogenated with 1 g of palladium-charcoal (10%) at 50° and under normal pressure. After hydrogen uptake has terminated, the catalyst is filtered off and the filtrate is evaporated in a vacuum. The residue crystallizes after the addition of ether. The crystals are filtered off by suction and washed with ether. The obtained 1-[p-(N'-methylureido)-phenoxy]-2-hydroxy-3-isopropylaminopropane melts at 152°–155° and has the formula

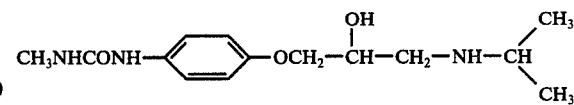

I claim:

1. A compound selected from the group consisting of an amine of the formula

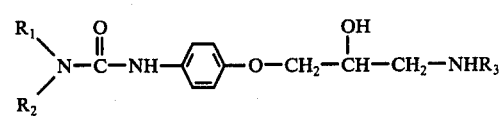

wherein $R_1$ denotes hydrogen, $R_2$ denotes cycloalkyl having 4 to 7 ring members and $R_3$ denotes lower alkyl and of therapeutically acceptable acid addition salts of such compounds.

* * * * *